(12) United States Patent
Lambert

(10) Patent No.: US 9,080,929 B2
(45) Date of Patent: Jul. 14, 2015

(54) PARALLEL BELT SAMPLER

(75) Inventor: Noel W. A. Lambert, Lower Belford (AU)

(73) Assignee: NEWCASTLE INNOVATION LIMITED, Callaghan (AU)

( * ) Notice: Subject to any disclaimer, the term of this patent is extended or adjusted under 35 U.S.C. 154(b) by 446 days.

(21) Appl. No.: 13/696,942

(22) PCT Filed: May 10, 2011

(86) PCT No.: PCT/AU2011/000541
§ 371 (c)(1),
(2), (4) Date: Nov. 8, 2012

(87) PCT Pub. No.: WO2011/140594
PCT Pub. Date: Nov. 17, 2011

(65) Prior Publication Data
US 2013/0047750 A1    Feb. 28, 2013

(30) Foreign Application Priority Data

May 10, 2010  (AU) ............................. 2010901979

(51) Int. Cl.
*G01N 1/20* (2006.01)
*B65G 47/52* (2006.01)
*B65G 47/58* (2006.01)

(52) U.S. Cl.
CPC *G01N 1/20* (2013.01); *B65G 47/52* (2013.01); *B65G 47/58* (2013.01); *G01N 2001/2021* (2013.01); *G01N 2001/2028* (2013.01)

(58) Field of Classification Search
CPC ............ G01N 1/20; G01N 2001/2021; G01N 2001/2028; B65G 47/52; B65G 47/58
USPC ............... 73/863.41, 863.43, 863.52–863.53, 73/863.56, 863.91–863.92; 177/245; 198/959
See application file for complete search history.

(56) References Cited

U.S. PATENT DOCUMENTS 1,860,107 A * 5/1932 Lien ......................... G01N 1/20
2,367,397 A * 1/1945 Harlow ...................... 73/863.92
(Continued)

FOREIGN PATENT DOCUMENTS

CN      201795940 U    4/2011
DE      3425004 A1 * 1/1986  ............... G01N 1/20
(Continued)

OTHER PUBLICATIONS

International Preliminary Report on Patentability in International Application No. PCT/US2011/000541 issued Nov. 13, 2012.
(Continued)

*Primary Examiner* — Thomas P Noland
(74) *Attorney, Agent, or Firm* — Marshall, Gerstein & Borun LLP

(57) ABSTRACT

Apparatus for sampling material being conveyed on a primary conveyor comprises a diverter arranged to divert material onto a sampling conveyor running alongside the primary conveyor where it can be weighed by a weightometer and elevated to a discharge point before falling into a falling-stream sample cutter. Material is then returned to the primary conveyor at by a return conveyor. Options include the use of an impact conveyor between the diverter and the sampling conveyor, and the configuration of the sampling conveyor with a wider belt running at a slower speed to improve accuracy.

9 Claims, 5 Drawing Sheets

(56) References Cited

U.S. PATENT DOCUMENTS

| | | | |
|---|---|---|---|
| 3,111,034 A * | 11/1963 | Hostetler | 73/863.91 X |
| 3,321,636 A * | 5/1967 | Karrer | 250/574 |
| 3,441,133 A * | 4/1969 | Miksitz | 209/139.2 |
| 3,524,352 A * | 8/1970 | Paul | 73/863.53 |
| 3,693,945 A * | 9/1972 | Brock | G01N 1/20 |
| 4,044,617 A * | 8/1977 | Mazzetti | 73/863.92 |
| 4,510,808 A * | 4/1985 | Neville | 73/433 |
| 4,790,196 A | 12/1988 | Gould | |
| 4,919,000 A | 4/1990 | Long | |
| 5,115,688 A | 5/1992 | van der Merwe et al. | |
| 5,133,982 A * | 7/1992 | Bodkin et al. | 426/231 |
| 5,385,058 A | 1/1995 | Krauss | |
| 6,438,189 B1 * | 8/2002 | Vourvopoulos | 376/159 |
| 6,559,655 B1 * | 5/2003 | Rosenthal et al. | 324/634 |
| 2002/0000131 A1 * | 1/2002 | Long et al. | 73/863.56 |
| 2009/0205446 A1 | 8/2009 | Lyman | |

FOREIGN PATENT DOCUMENTS

| | | | | |
|---|---|---|---|---|
| GB | 1226196 A | * | 8/1974 | G01N 1/20 |
| JP | 58223715 A | * | 12/1983 | 177/245 |
| JP | 02038942 A | * | 2/1990 | G01N 1/04 |
| JP | H0216853 B2 | * | 4/1990 | G01N 1/04 |
| JP | 2009008552 A | * | 1/2009 | G01N 35/04 |
| RU | 2409809 C1 | | 1/2011 | |
| WO | WO-89/11089 A1 | | 11/1989 | |
| WO | WO 2004008260 A1 | * | 1/2004 | G05B 13/02 |

OTHER PUBLICATIONS

International Search Report in PCT/AU2011/000541 mailed Jul. 11, 2011 (2 pages).

* cited by examiner

PARALLEL BELT SAMPLER

FIELD OF THE INVENTION

This invention relates to a parallel belt sampler and has been devised particularly though not solely for sampling minerals being conveyed on a belt conveyor from a mine into a processing plant.

BACKGROUND OF THE INVENTION

Billions of tonnes of materials are transferred by conveyor every year and most of this needs to be sampled for quality control, plant regulation, or for checking that sales obligations are met. In many instances, the mass of this material must also be accurately measured.

Falling-stream samplers are the most accurate way to sample the material on a conveyor belt but these samplers are difficult to retrofit to existing conveyor belt situations and often have access and availability problems.

Cross-belt samplers are a much cheaper alternative to retrofit, and are often installed in new plant, but are not as accurate as falling-stream samplers.

Weightometers are often placed under belt conveyors to measure the mass of materials being conveyed, but they often have accuracy problems due to the length, speed and tension in the conveyor belt.

It is a further problem of falling-stream samplers that they require significant vertical space between the conveyor discharge point and any other structure to allow the falling-stream cutter to be placed and to move. Due to this height requirement, it is very difficult and expensive to retrofit falling-stream samplers into existing plants. They are often placed at a great height above loading bins or plant feed entry points causing problems with access and potential safety problems. It also means that often falling-stream samplers in these locations are not given the maintenance work that they should due to safety and access problems.

Falling-stream samplers also require that the conveyor be stopped whilst maintenance work is carried out and this interferes with production.

SUMMARY OF THE INVENTION

The present invention therefore provides apparatus for sampling material being conveyed on a primary conveyor, the apparatus including:

a diverter arranged to continuously divert material to one side of the primary conveyor;

a sampling conveyor running alongside the primary conveyor and arranged to receive material diverted by the diverter;

a primary sampler arranged to select and sample material falling from a discharge end of the sampling conveyor; and a return conveyor arranged to return non-selected material falling from the discharge end of the sampling conveyor to the primary conveyor.

Preferably, the primary conveyor, the sampling conveyor and the return conveyor all comprise belt conveyors.

Preferably, the diverter comprises a tripper that can be activated to raise one side of the primary conveyor belt to divert all of the material from the primary conveyor to the sampling conveyor.

In some forms of the invention, materials diverted by the diverter are firstly diverted onto an impact conveyor with or without the aid of chutes arranged to direct material received from the diverter.

Preferably, the sampling conveyor is wider than the primary conveyor so that it may be operated at a lower speed than the primary conveyor while still maintaining the same flow rate of material on the primary conveyor.

Preferably, the sampling conveyor incorporates a weightometer positioned below the belt of the sampling conveyor.

Preferably, the primary sampler comprises a falling-stream sampling cutter located beneath the discharge end of the sampling conveyor.

Preferably, the return conveyor is inclined and angled so as to receive the non-selected material falling from the discharge end of the sampling conveyor and to elevate that material to a discharge point where it can fall back onto the primary conveyor.

BRIEF DESCRIPTION OF THE DRAWINGS

Notwithstanding any other forms that may fall within its scope, one preferred form of the invention will not be described with reference to the accompanying drawings in which.

DETAILED DESCRIPTION OF THE PREFERRED EMBODIMENT OF THE INVENTION

The form of the invention now described and shown diagrammatically in the accompanying drawings is particularly intended for the sampling of mined materials such as coal as it is transported on a primary conveyor belt (1) to a destination which may, for example, be a processing plant.

The primary conveyor 1 is provided with a diverter in the form of a tripper 2 which is typically a standard piece of equipment that diverts all the material from the primary conveyor 1 to one side of that conveyor. This may be done via a chute 8 (FIG. 3) or any other suitable means. The tripper is typically activated by hydraulic or pneumatic rams beneath the conveyor which lift a set of conveyor support rollers on one side of the conveyor to divert the material.

Figure 1:
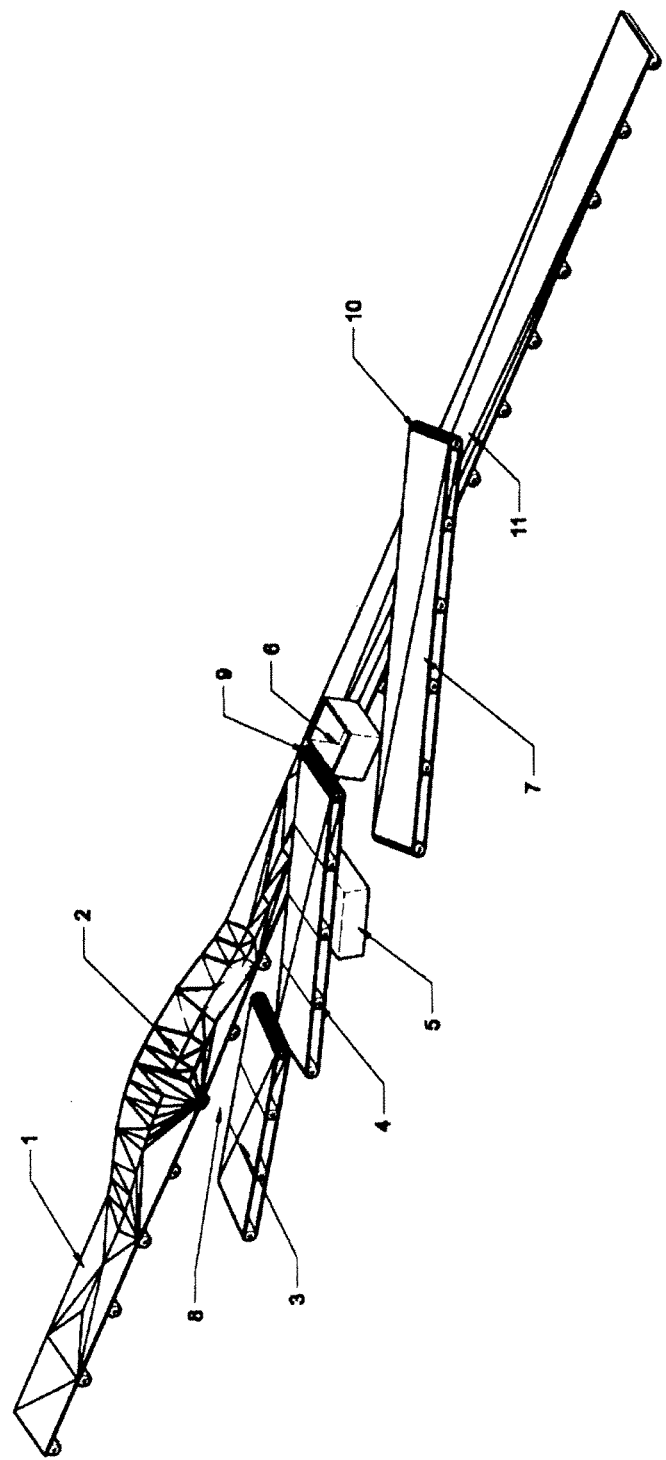
FIG. 1 is a diagrammatic perspective view of a parallel belt sampler according to the invention.
Figure 2:
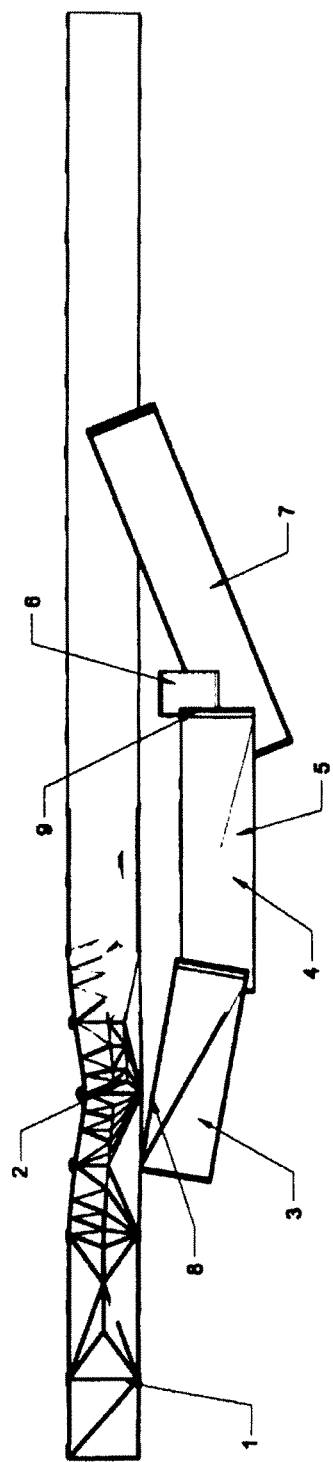
FIG. 2 is a plan view of the apparatus as shown in FIG. 1.
Figure 4:
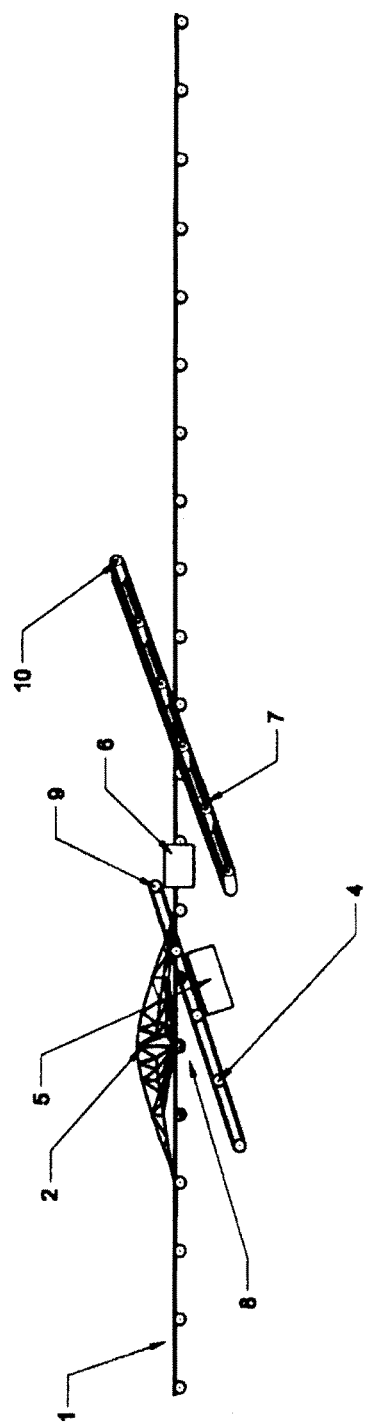
FIG. 4 is a similar view to FIG. 3 showing the apparatus without the use of an impact conveyor.

The diverted material typically lands on an impact conveyor 3 from where it is conveyed to a sampling conveyor 4 typically running alongside the primary conveyor 1 as can be clearly seen in FIGS. 1 and 2. The use of the impact conveyor 3 is optional and it may be omitted as shown in the embodiment in FIG. 4 but it is typically incorporated in order to avoid deviations in the running speed of the sampling conveyor 4 or impact upon a weightometer 5 which might affect the accuracy of the overall system.

The sampling conveyor 4 is provided with a weightometer 5 typically located beneath the belt of the sampling conveyor and operable in the normal manner to determine the mass of the material passing along the sampling conveyor 4.

At the discharge end 9 of the sampling conveyor 4 a falling-stream sample cutter 6 is located arranged to select and sample material falling from the discharge end of the sampling conveyor 4. The falling-stream sampling cutter typically includes a bucket movable along transverse rails beneath the discharge stream from the sampling conveyor 4 in the manner which is well-known in the art.

Material that is not collected in the bucket of the falling-stream sample cutter lands on a return conveyor 7 where it is transported upwardly as can be seen in FIGS. 1, 3, 4 and 5, and transversely as can be seen in FIG. 2 to a discharge point 10 from where the material is returned to the primary conveyor 1 at point 11. Once again, if desired or necessary, chutes may be provided at this point to ensure that the material is correctly delivered to the primary conveyor 1.

By diverting the material to be sampled from the primary conveyor 1 onto a separate or parallel sampling conveyor 4, a number of advantages are able to be gained.

The entire sampler can be provided as a separate and discrete piece of apparatus which can be positioned alongside an existing primary conveyor 1 without any interruption to the operation of that conveyor. The only modification to the primary conveyor is the incorporation of the diverter or tripper 2 which is a commonly available piece of apparatus easily able to be supplied and fitted to the primary conveyor.

Figure 3:
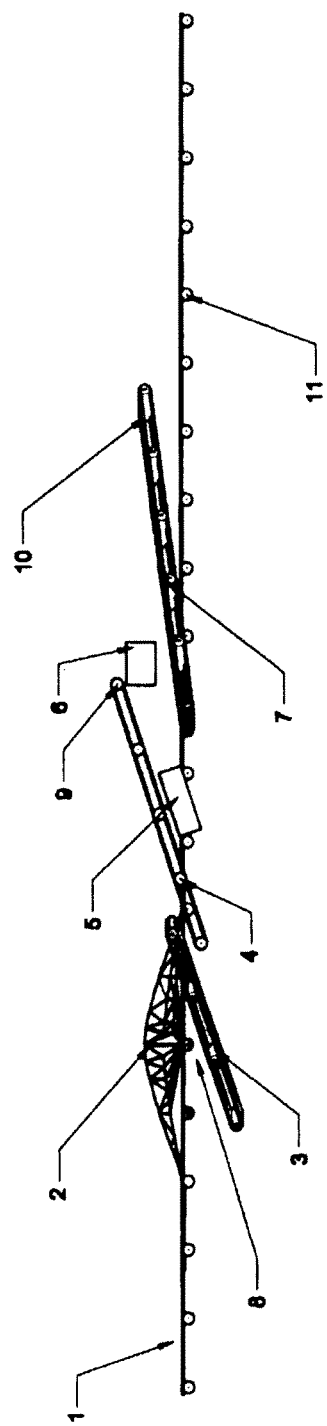
FIG. 3 is a diagrammatic side view of the apparatus shown in FIG. 1.

Because elevation of the material to be sampled can be gained through any one or more of the impact conveyor 3, the sampling conveyor 4 and the return conveyor 7 as can be clearly seen in FIG. 3, it is possible to operate the primary conveyor 1 in a horizontal or gently inclined position while still obtaining the height necessary between the discharge end 9 of the sampling conveyor and the lower end of the return conveyor 7 in order to allow for operation of the falling-stream sampler 6.

Figure 5:
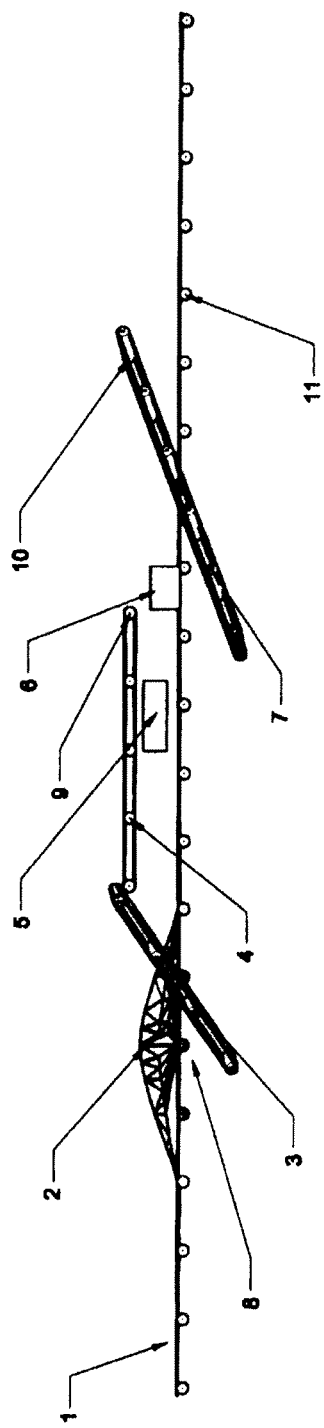
FIG. 5 is a similar view to FIG. 3 showing an arrangement where the sampling conveyor is operated in a substantially horizontal orientation.

In some situations, it may be desired to operate the sampling conveyor in a level configuration and this can be easily be provided for using apparatus according to the invention as shown in FIG. 5. In this instance, the height required to operate the falling-stream sampler is obtained by the inclination of the impact conveyor 3.

It is a problem with existing samplers that the belt speed of the primary conveyor 1 is often too high to allow accurate sampling. Primary conveyors will often operate at a belt speed of between 4-6 m/s whereas it is recognised that weightometers of the type placed at 5 and also falling-stream samplers work most accurately at velocities in the order of 1-2 m/s.

By making the sampling conveyor 4 significantly wider than the primary conveyor 1 as can be clearly seen in FIG. 2, the speed of the sampling conveyor can be significantly reduced while still maintaining the same throughput of material from the primary conveyor 1. For example, if the primary conveyor is operating at 6 m/s and the sampling conveyor is 3 times wider than the primary conveyor 1, then the sampling conveyor 4 need only operate at 2 m/s in order to maintain the flow of material from the primary conveyor 1. This feature allows for significantly more accurate operation of the falling-stream sampler 6 and the weightometer 5.

The provision of an impact conveyor 3 also allows the sampling conveyor 4 to operate at a constant speed without being significantly affected by the inertia of material from the primary conveyor 1 being diverted by the tripper 2. There are however some instances where this may not be a significant factor and the impact conveyor 3 may be omitted as shown in the configuration represented in FIG. 4.

Because the parallel sampling system according to the invention is a compact stand-alone unit that can be positioned at ground level directly alongside the primary conveyor 1, it is cheaper and safe to maintain and can also be connected to an existing system in a relatively short time thus minimising downtime for installation.

Where it is necessary to perform stop belt sampling, the tripper 2 can simply be deactivated allowing the continuous operation of the primary conveyor 1 while the sampling conveyor 4 can be stopped to perform stop belt sampling.

In this manner, the parallel sampling system according to the invention is more accurate in terms of sampling and mass flow measurement than existing sampling and flow measurement systems, is cheaper and safer to maintain and will cost less than existing systems, whether it is fitted to a new system or to a retrofit.

The invention claimed is:

1. An apparatus for sampling material being conveyed on a primary conveyor, the apparatus including:
    a diverter arranged to divert material to one side of the primary conveyor;
    a sampling conveyor running alongside the primary conveyor and arranged to receive material diverted by the diverter;
    a primary sampler arranged to select and sample material falling from a discharge end of the sampling conveyor; and
    a return conveyor arranged to return non-selected material falling from the discharge end of the sampling conveyor to the primary conveyor.

2. An apparatus for sampling material as claimed in claim 1, wherein the primary conveyor, the sampling conveyor and the return conveyor all comprise belt conveyors.

3. An apparatus for sampling material as claimed in claim 2, wherein the diverter comprises a tripper that can be activated to raise one side of the primary conveyor belt to divert all of the material from the primary conveyor to the sampling conveyor.

4. An apparatus for sampling material as claimed in claim 1, wherein materials diverted by the diverter are firstly diverted onto an impact conveyor before being delivered to the sampling conveyor.

5. An apparatus for sampling material as claimed in claim 4, wherein materials are diverted onto the impact conveyor with the aid of one or more chutes arranged to direct material received from the diverter.

6. An apparatus for sampling material as claimed in claim 1, wherein the sampling conveyor is wider than the primary conveyor so that it may be operated at a lower speed than the primary conveyor while still maintaining the same flow rate of material on the primary conveyor.

7. An apparatus for sampling material as claimed in claim 6, wherein the sampling conveyor incorporates a weightometer arranged to weigh material passing over the sampling conveyor.

8. An apparatus for sampling material as claimed in claim 1, wherein the sampling conveyor incorporates a weightometer arranged to weigh material passing over the sampling conveyor.

9. An apparatus for sampling material as claimed in claim 1, wherein the primary sampler comprises a falling stream sample cutter.

* * * * *